United States Patent
Johns

(10) Patent No.: US 8,501,659 B2
(45) Date of Patent: Aug. 6, 2013

(54) PROCESSES FOR THE PREPARATION OF ARYLAMINE COMPOUNDS

(75) Inventor: Adam M. Johns, Burbank, CA (US)

(73) Assignee: Univation Technologies, LLC, Houston, TX (US)

( * ) Notice: Subject to any disclaimer, the term of this patent is extended or adjusted under 35 U.S.C. 154(b) by 15 days.

(21) Appl. No.: 13/126,202

(22) PCT Filed: Oct. 21, 2009

(86) PCT No.: PCT/US2009/061453
§ 371 (c)(1),
(2), (4) Date: Apr. 27, 2011

(87) PCT Pub. No.: WO2010/053696
PCT Pub. Date: May 14, 2010

(65) Prior Publication Data
US 2011/0207599 A1     Aug. 25, 2011

Related U.S. Application Data

(60) Provisional application No. 61/198,852, filed on Nov. 10, 2008.

(51) Int. Cl.
*B01J 31/02* (2006.01)
*C07C 209/00* (2006.01)
*C07C 213/08* (2006.01)

(52) U.S. Cl.
USPC ............ 502/167; 564/368; 564/367; 564/346

(58) Field of Classification Search
None
See application file for complete search history.

(56) References Cited

U.S. PATENT DOCUMENTS

| 3,914,311 A | 10/1975 | Coulson |
| 5,576,460 A | 11/1996 | Buchwald et al. |
| 5,929,281 A | 7/1999 | Nishiyama et al. |
| 6,235,938 B1 * | 5/2001 | Hartwig et al. ............... 564/407 |
| 6,518,444 B1 | 2/2003 | McConville et al. |
| 2005/0182212 A1 * | 8/2005 | Wenzel et al. ............... 526/161 |

FOREIGN PATENT DOCUMENTS

| WO | WO 2005/082948 | 9/2005 |
| WO | WO 2007/109365 | 9/2007 |

OTHER PUBLICATIONS

Beletskaya et al. Eur. J. Org. Chem. 2005, 261-280.*
Reddy et al. J. Org. Chem., 73, 3047-3062.*
Shen, Q. et al., ["(CyPF-tBU)PdC12]: An Air-Stable, One-Component, Highly Efficient Catalyst for Amination of Heteroaryl and Aryl Halides" Organic Letters, vol. 10, No. 18, Aug. 21, 2008, pp. 4109-4112.
Shen Q et al: "Palladium-catalyzed coupling of ammonia and lithium amide with aryl halides" Journel of the American Chemical Society, American Chemical Society, New York, UA LNKD—DOI: 10.1021/ja064005t, vol. 128, No. 31, Jul. 12, 2006, pp. 10028-10029.
Shen, Q et al.,, Highly Reactive, General, and Long-Lived Catalysts for Coupling Heteroaryl and Aryl Chlorides witih Primary Nitrogen Nucleophiles, Angew. Chem., Int. Ed.; 2005, 44, 1371-1375.

* cited by examiner

*Primary Examiner* — Yun Qian
(74) *Attorney, Agent, or Firm* — Kristina Leavitt; Jennifer A. Schmidt; Leandro Arechederra, III

(57) ABSTRACT

A process for the preparation of N-arylamine compounds, the process including: reacting a compound having an amino group with an acylating compound in the presence of a base and a transition metal catalyst under reaction conditions effective to form an N-arylamine compound; wherein the transition metal catalyst comprises a complex of a Group 8-10 metal and at least one chelating ligand comprising (R)-(−)-1-[(S)-2-dicyclohexylphosphino]-ferrocenyl]ethyldi-t-butylphosphine.

4 Claims, 1 Drawing Sheet

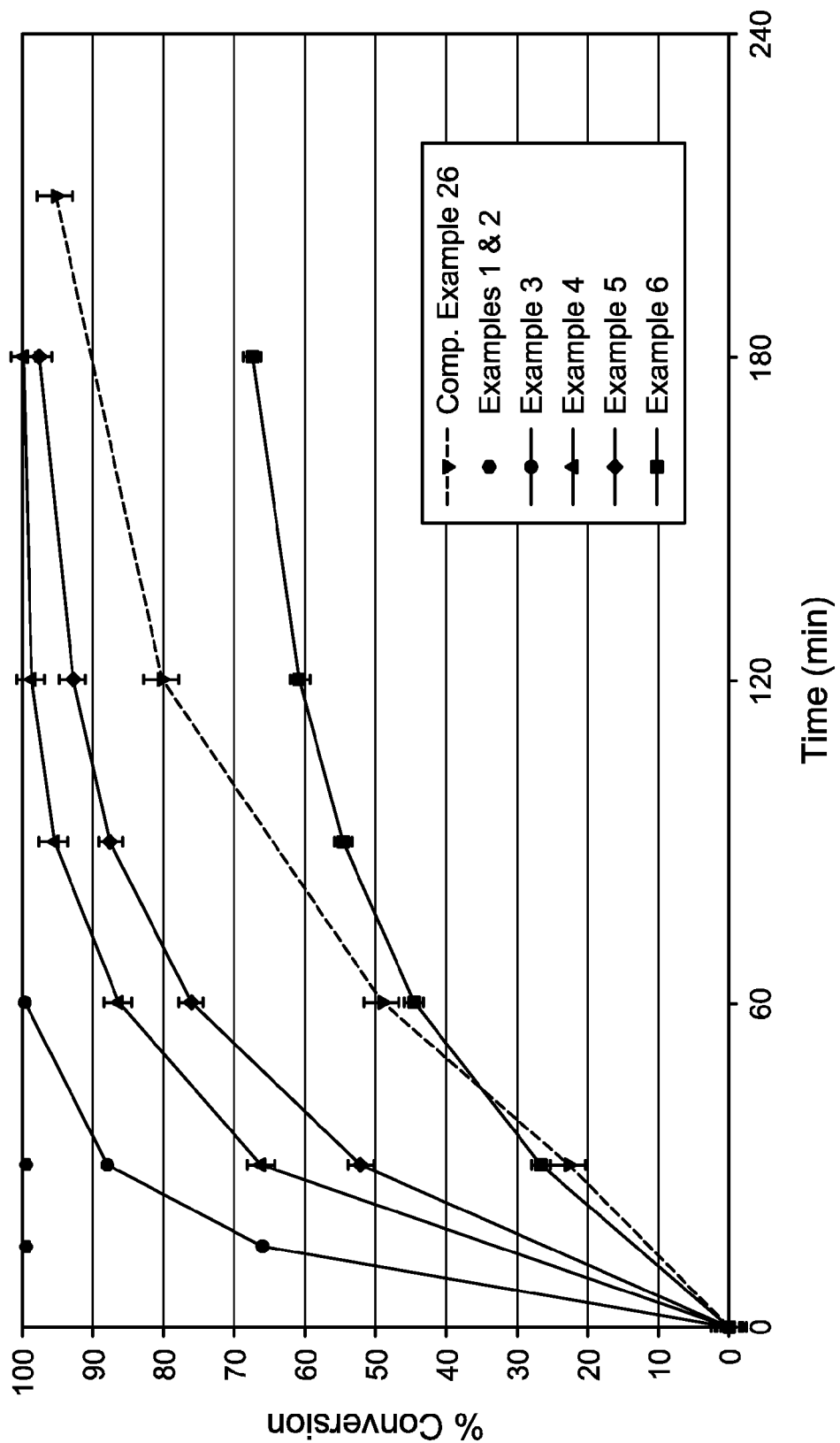

PROCESSES FOR THE PREPARATION OF ARYLAMINE COMPOUNDS

CROSS-REFERENCE TO RELATED APPLICATIONS

This application is a National Stage application under 36 U.S.C. §371 of International Application No. PCT/US2009/061453, filed Oct. 21, 2009, that claims the benefit of Ser. No. 61/198,852, filed Nov. 10, 2008, the disclosures of which are incorporated by reference in their entireties.

FIELD OF THE INVENTION

In one aspect, embodiments disclosed herein relate to the preparation of arylamines. In another aspect, embodiments disclosed herein relate to the preparation of Group 15 atom and metal catalyst compounds.

BACKGROUND

N-arylamines compounds are important substructures in natural products and industrial chemicals, such as pharmaceuticals, dyes, and agricultural products. N-arylamines are useful for screening for pharmaceutical and biological activity and in the preparation of commercial polymers. It would be advantageous to prepare N-arylamine compounds from arylating compounds such as aryl halides and/or aryl tosylates because aryl halides are generally inexpensive and readily available, while aryl tosylates are easily prepared from phenols. However, to date, methods of producing N-arylamines are inefficient or economically unattractive. Many known processes that generate an aryl-nitrogen bond must be performed under harsh reaction conditions, or must employ activated substrates which are sometimes not available. Examples of procedures that generate aryl amine compounds include nucleophilic substitution of aryl precursors and synthesis of aryl amines via copper-mediated Uhlmann condensation reactions.

The commercialization of metallocene polyolefin catalysts has led to widespread interest in the design and preparation of other catalysts and catalyst systems, particularly for use in economical gas and slurry phase processes. Anionic, multidentate heteroatom ligands have received attention in polyolefins catalysis. Notable classes of bidentate anionic ligands which form active polymerization catalysts include N—N⁻ and N—O⁻ ligand sets. Examples of these types of catalysts include amidopyridines and polyolefin catalysts based on hydroxyquinolines.

U.S. Pat. No. 5,576,460 (the '460 patent) discloses two synthesis routes to preparing arylamine compounds. The first route includes reaction of a metal amide comprising a metal selected from the group consisting of tin, boron, zinc, magnesium, indium and silicon, with an aromatic compound comprising an activated substituent in the presence of a transition metal catalyst to form an arylamine. The second route utilizes an amine rather than a metal amide. The '460 patent teaches that this reaction be conducted at a temperature of less than about 120° C. and is drawn to the use of the arylamine as an intermediate in pharmaceutical and agricultural applications.

U.S. Pat. No. 5,929,281 discloses the preparation of heterocyclic aromatic amines in the presence of a catalyst system comprising a palladium compound and a tertiary phosphine and the preparation of arylamines in the presence of a catalyst system comprising a palladium compound and a trialkylphosphine.

U.S. Pat. No. 3,914,311 discloses a low temperature method of preparing an arylamine by the reaction of an amine with an aromatic compound having a displaceable activated substituent at temperatures as low as 25° C. in the presence of nickel catalyst and a base.

Other patents discussing N-arylamine compounds may include U.S. Pat. Nos. 6,235,938 and 6,518,444, among others, as well as references such as, Shen, Q., Shekhar, S, Stambuli, J. P., Hartwig, J. F., *Angew. Chem., Int. Ed.;* 2005, 44, 1371-1375.

A need exists for a general and efficient process of synthesizing N-arylamine compounds from readily available arylating compounds. The discovery and implementation of such a method would simplify the preparation of commercially significant organic N-aryl amines and would enhance the development of novel polymers and pharmacologically active compounds.

SUMMARY

In one aspect, embodiments disclosed herein relate to a process for the preparation of N-aryl amine compounds, the process including: reacting a compound having an amino group with an arylating compound in the presence of a base and a transition metal catalyst under reaction conditions effective to form an N-aryl amine compound; wherein the transition metal catalyst comprises a complex of a Group 8-10 metal and at least one chelating ligand comprising (R)-(−)-1-[(S)-2-dicyclohexylphosphino]-ferrocenyl]ethyldi-t-butylphosphine.

In another aspect, embodiments disclosed herein relate to a process for preparing a Group 15 atom and metal catalyst compound, the process including: a) preparing a ligand comprising an N-aryl amine compound by reacting a compound having an amino group with an arylating compound in the presence of a base and a transition metal catalyst under reaction conditions effective to form an N-aryl amine compound, wherein the transition metal catalyst comprises a Group 8 metal and at least one chelating ligand comprising (R)-(−)-1-[(S)-2-dicyclohexylphosphino]-ferrocenyl]ethyldi-t-butylphosphine; and b) combining the ligand prepared in step a) with a compound represented by the formula $M^nX_n$, where M is a Group 3 to 14 metal, n is the oxidation state of M, and X is an anionic group.

BRIEF DESCRIPTION OF THE DRAWING

FIG. 1 is a graphical comparison of the performance of catalysts according to embodiments disclosed herein and comparative catalysts for the production of N-aryl amines.

DETAILED DESCRIPTION

Before the present compounds, components, compositions, and/or methods are disclosed and described, it is to be understood that unless otherwise indicated this invention is not limited to specific compounds, components, compositions, reactants, reaction conditions, ligands, metallocene structures, or the like, as such may vary, unless otherwise specified. It is also to be understood that the terminology used herein is for the purpose of describing particular embodiments only and is not intended to be limiting.

It must also be noted that, as used in the specification and the appended claims, the singular forms "a," "an" and "the" include plural referents unless otherwise specified. Thus, for example, reference to "a leaving group" as in a moiety "substituted with a leaving group" includes more than one leaving group, such that the moiety may be substituted with two or more such groups. Similarly, reference to "a halogen atom" as in a moiety "substituted with a halogen atom" includes more than one halogen atom, such that the moiety may be substituted with two or more halogen atoms, reference to "a substituent" includes one or more substituents, reference to "a ligand" includes one or more ligands, and the like.

As used herein, all reference to the Periodic Table of the Elements and groups thereof is to the NEW NOTATION published in HAWLEY'S CONDENSED CHEMICAL DICTIONARY, Thirteenth Edition, John Wiley & Sons, Inc., (1997) (reproduced there with permission from IUPAC), unless reference is made to the Previous IUPAC form noted with Roman numerals (also appearing in the same), or unless otherwise noted.

In one aspect, embodiments disclosed herein relate to the preparation of N-aryl amine compounds. In another aspect, embodiments disclosed herein relate to the preparation of Group 15 atom and metal catalyst compounds.

Preparation of N-Aryl Amine Ligands (Ligands YLZ and YL'Z)

N-aryl amine compounds may be synthesized according to embodiments disclosed herein from a compound having an amino group, and an arylating compound. The term "aryl" is defined herein as a compound whose molecules have the ring structure characteristic of benzene, naphthalene, phenanthroline, anthracene, heterocyclic, and the like. "Arylating compound" is defined as a compound which provides an aryl substituent in an organic reaction. "N-Aryl amine compounds" are those compounds in which a nitrogen atom of the compound is substituted with an aryl group.

The reaction may be performed in the presence of a base and a Group 8-10 transition metal catalyst. One example of a reaction between an arylating compound and an amine to produce an N-aryl amine compound may be represented by reaction (I):

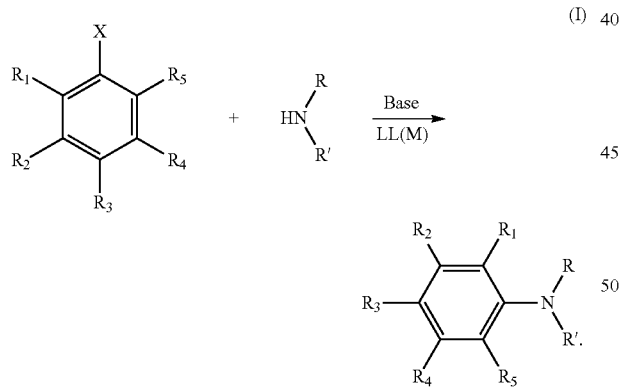

Briefly, in reaction (I), an arylating compound is reacted with an amine compound in the presence of a base and a Group 8-10 transition metal (M) complex including a chelating ligand (LL) to form an N-aryl amine compound. Each of these reactions and their components are described in more detail below.

The transition metal catalyst according to embodiments disclosed herein is a Group 8-10 transition metal complex of ((R)-(–)-1-[(S)-2-dicyclohexylphosphino)-ferrocenyl]ethyldi-t-butylphosphine), herein abbreviated as CyPF-t-Bu. In certain embodiments, the Group 8-10 transition metal comprises at least one of palladium, platinum, and nickel. In some embodiments, the Group 8-10 transition metal is palladium. It has been found that the palladium complex of CyPF-t-Bu may beneficially yield higher conversions and selectivity than prior palladium catalysts disclosed for production of N-aryl amine compounds, thus allowing for efficient production of N-aryl amine compounds, an important class of compounds which are particularly significant in the development of pharmacologically active compounds and processing of polymers and oligomers.

N-aryl amine compounds may be synthesized according to embodiments disclosed herein by reaction of an amine-containing compound, such as a primary amine or a secondary amine, with an arylating compound in the presence of a base and a Group 8-10 transition metal complex of CyPF-t-Bu under reaction conditions effective to form an N-aryl amine compound. CyPF-t-Bu may be represented by formula (II).

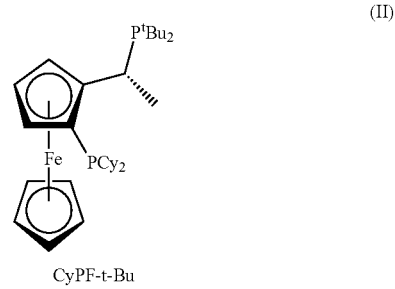

CyPF-t-Bu

The arylating compound used in the process of the present invention may be any arylating compound of the formula (III):

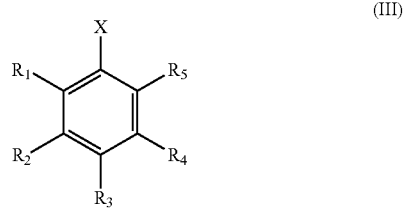

In formula (III), X may be any halide atom (F, Cl, Br, I), or any sulfur-containing leaving group (e.g., triflate, sulfonate, tosylate, and the like) known in the art. Chlorides are especially preferred in the process of the present invention. $R_1$, $R_2$, $R_3$, $R_4$, and $R_5$ are independently selected from H; CN; alkyl, such as methyl, ethyl, propyl, n-butyl, t-butyl, and the like; alkoxy, vinyl, alkenyl, formyl; $CF_3$; $CCl_3$; halide, $C_6H_5$; amide such as $C(O)N(CH_3)_2$, $C(O)N(CH_2CH_3)_2$, $C(O)N(CH_2CH_2CH_3)_2$, and the like; acyl, such as $C(O)$—$C_6H_5$, and the like; ester, amino, thioalkoxy, phosphino, and the like. Arylating compound may also be a heterocyclic aromatic compound such as an azole or azole derivative, aryl phosphates, aryl trifluoroacetates, and the like. Alternatively, the arylating compound may be the process of claim 1, wherein said arylating compound any aromatic or heteroaromatic halide, such as an aromatic or heteroaromatic chloride.

Preferred arylating compounds used in the process of the invention may include aryl bromides such as chlorobenzene, 4-chloro-benzonitrile, 4-chloro-t-butyl benzene, 3-chloromethoxy benzene, 2-chloro toluene, p-formyl phenyl chloride, p-$CF_3$ phenyl chloride, p-phenyl phenyl chloride, p-C(O)N(CH_2CH_3)_2 phenyl chloride, and p-C(O)—$C_6H_5$ phenyl chloride.

In some embodiments, the arylating compound may include at least one of 2,3,4,5,6-pentamethylbromobenzene (PMBB) and 2,4,6-trimethylbromobenzene (TMBB). In some embodiments, the arylating compound may include 2,3,4,5,6-pentamethylbromobenzene. In other embodiments, the arylating compound may include 2,4,6-trimethylbromobenzene.

According to the method of the invention, amine-containing compounds include primary amine (e.g., R or R' is hydrogen) or secondary amine compounds (e.g., R and R' are not H). Examples of useful primary amines include aniline (NH$_2$Ph) and aminobutane (NH$_2$Bu). Examples of useful secondary amines include morpholine (C$_4$H$_9$NO) and piperidine (C$_5$H$_{11}$N). Other useful amines may include diethylenetriamene, 1,5 diaminopentane, and 2,2'-oxydiethylamine, among others. Such amines may be used alone or in combination.

The base shown in Scheme I is required for the process of the invention. Any base may be used so long as the process of the invention proceeds to the N-aryl amine product. It may be important in this regard that the base does not displace all of the chelating ligands on the catalyst. Nuclear magnetic resonance, infrared, and Raman spectroscopies, for example, are useful in determining whether the chelating ligands remain bonded to the Group 8-10 metal or whether the ligands have been displaced by the base.

Non-limiting examples of suitable bases include alkali metal hydroxides, such as sodium and potassium hydroxides; alkali metal alkoxides, such as sodium t-butoxide; metal carbonates, such as potassium carbonate, cesium carbonate, and magnesium carbonate; phosphates; alkali metal aryl oxides, such as potassium phenoxide; alkali metal amides, such as lithium amide; tertiary amines, such as triethylamine and tributylamine; (hydrocarbyl)ammonium hydroxides, such as benzyltrimethylammonium hydroxide and tetraethylammonium hydroxide; and diaza organic bases, such as 1,8-diazabicyclo[5.4.0]-undec-7-ene and 1,8-diazabicyclo-[2.2.2.]-octane. Preferably, the base is an alkali hydroxide or alkali alkoxide, more preferably, an alkali alkoxide, and most preferably, an alkali metal C$_{1-10}$ alkoxide.

The quantity of base which is used can be any quantity which allows for the formation of the N-aryl amine product. Preferably, the molar ratio of base to arylating compound ranges from about 1:1 to about 3:1, and more preferably between about 1:1 and 2:1.

In one particular embodiments, the amine compound may be diethylenetriamine and the arylating compound may be 2,3,4,5,6-pentamethylbromobenzene to form N$^1$-(2,3,4,5,6-pentamethylphenyl)-N$^2$-(2-(2,3,4,5,6-pentamethylphenylamino)ethyl)ethane-1,2-diamine, where the reaction, represented by formula (IV), is performed in the presence of the above described palladium complex with CyPF-t-Bu as the ligand (L).

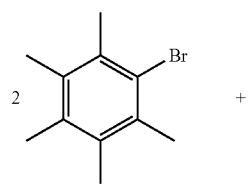

(IV)

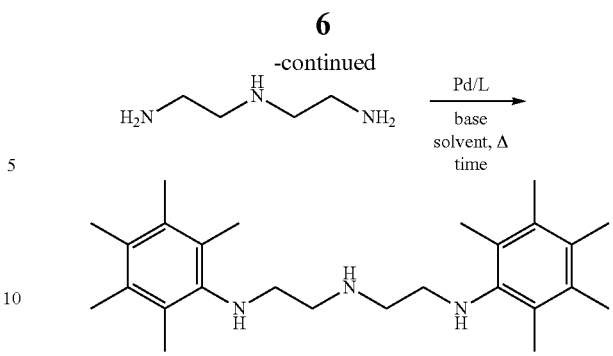

The transition metal catalyst may be synthesized first and thereafter employed in the arylation process. Alternatively, the catalyst can be prepared in situ in the arylation reaction mixture. If the latter is used, then a palladium catalyst precursor compound and the chelating ligand (CyPF-tBu) are independently added to the reaction mixture wherein formation of the transition metal catalyst occurs in situ. Suitable precursor compounds include alkene and diene complexes of palladium, preferably, di(benzylidene)acetone (dba) complexes of palladium, as well as, monodentate phosphine complexes of the palladium, and palladium carboxylates. In the presence of the chelating ligand, in situ formation of the transition metal catalyst occurs. Non-limiting examples of suitable precursor compounds include [bis-di(benzylidene)acetone]palladium (0), tetrakis-(triphenylphosphine)-palladium (0), tris-[di(benzylidene)acetone]palladium (0), tris-[di(benzylidene)acetone]-dipalladium (0), palladium acetate, and the analogous complexes of iron, cobalt, nickel, ruthenium, rhodium, osmium, iridium, and platinum. Any of the aforementioned catalyst precursors may include a solvent of crystallization. Group 8-10 metals supported on carbon, preferably, palladium on carbon, can also be suitably employed as a precursor compound. In certain embodiments, the catalyst precursor compound is palladium acetate.

The quantity of transition metal catalyst which is employed in the process of this invention is any quantity which promotes the formation of the N-aryl product. Generally, the quantity is a catalytic amount, which means that the catalyst is used in an amount which is less than stoichiometric relative to the unsaturated organic sulfonate. Typically, the transition metal catalyst ranges from about 0.01 to about 20 mole percent, based on the number of moles of the compound having at least one unsaturated nitrogen atom used in the reaction. Preferably, the quantity of transition metal catalyst ranges from about 1 to about 10 mole percent, and more preferably from about 3 to about 8 mole percent, based on the moles of the unsaturated nitrogen-containing compound.

The process described herein may be conducted in any conventional reactor designed for catalytic processes. Continuous, semi-continuous, and batch reactors can be employed. If the catalyst is substantially dissolved in the reaction mixture as in homogeneous processes, then batch reactors, including stirred tank and pressurized autoclaves, can be employed. If the catalyst is anchored to a support and is substantially in a heterogeneous phase, then fixed-bed and fluidized bed reactors can be used. In the typical practice of this invention the compound having an amino group, arylating compound, base, and catalyst are mixed in batch, optionally with a solvent, and the resulting mixture is maintained at a temperature and pressure effective to prepare the N-arylated product.

Any solvent can be used in the process of the invention provided that it does not interfere with the formation of the N-aryl amine product. Both aprotic and protic solvents and combinations thereof are acceptable. Suitable aprotic solvents include, but are not limited to, aromatic hydrocarbons, such as toluene and xylene, chlorinated aromatic hydrocarbons, such as dichlorobenzene, and ethers, such as tetrahydrofuran. Suitable protic solvents include, but are not limited to, water and aliphatic alcohols, such as ethanol, isopropanol, and cyclohexonol, as well as glycols and other polyols. The amount of solvent which is employed may be any amount, preferably an amount sufficient to solubilize, at least in part, the reactants and base. A suitable quantity of solvent typically ranges from about 1 to about 100 grams solvent per gram reactants. Other quantities of solvent may also be suitable, as determined by the specific process conditions and by the skilled artisan.

Catalysts may be used to prepare N-aryl amines according to embodiments disclosed herein at any effective amount. In some embodiments, the transition metal catalyst is present during the arylation reaction at a concentration in the range from about 0.01 to about 1.25 mole percent, based on a total amount of the compound having an amino group, the arylating compound, and the transition metal catalyst. In other embodiments, the transition metal catalyst is present during the arylation reaction at a concentration in the range from about 0.03 to about 1.0 mole percent, based on a total amount of the compound having an amino group, the arylating compound, and the transition metal catalyst; from about 0.03 to about 0.5 mole percent, based on a total amount of the compound having an amino group, the arylating compound, and the transition metal catalyst in other embodiments; and from about 0.05 to about 0.1 mole percent, based on a total amount of the compound having an amino group, the arylating compound, and the transition metal catalyst in yet other embodiments.

Generally, the reagents may be mixed together or added to a solvent in any order. Air is preferably removed from the reaction vessel during the course of the reaction, however this step is not always necessary. If it is desirable or necessary to remove air, the solvent and reaction mixture can be sparged with a non-reactive gas, such as nitrogen, helium, or argon, or the reaction may be conducted under anaerobic conditions. The process conditions can be any operable conditions which yield the desired N-aryl product. Beneficially, the reaction conditions for this process are mild. For example, a preferred temperature for the process of the present invention ranges from about ambient, taken as about 22° C., to about 150° C., and preferably, from about 80° C. to about 110° C. The process may be run at subatmospheric pressures if necessary, but typically proceeds sufficiently well at about atmospheric pressure. The process is generally run for a time sufficient to convert as much of the unsaturated nitrogen-containing compound to product as possible. Typical reaction times range from about 30 minutes to about 24 hours, but longer times may be used if necessary.

The N-arylated amine product can be recovered by conventional methods known to those skilled in the art, including, for example, distillation, crystallization, sublimation, and gel chromatography. The yield of product will vary depending upon the specific catalyst, reagents, and process conditions used. For the purposes of this invention, "yield" is defined as the mole percentage of N-aryl amine product recovered, based on the number of moles of unsaturated nitrogen-containing compound employed. Typically, the yield of N-aryl amine product is greater than about 25 mole percent. Preferably, the yield of N-aryl amine product is greater than about 60 mole percent, and more preferably, greater than about 80 mole percent.

Group 15 Atom and Metal Catalyst Compound

The Group 15 atom and metal catalyst compounds, which may be prepared by methods disclosed herein, generally include a Group 3 to 14 metal atom, preferably a Group 3 to 7, more preferably a Group 4 to 6, and even more preferably a Group 4 metal atom, bound to at least one leaving group and also bound to at least two Group 15 atoms, at least one of which is also bound to a Group 15 or 16 atom through another group. The Group 15 atoms of the catalyst compound are also bound to a Group 15 or 16 atom through another group which may be a $C_1$ to $C_{20}$ hydrocarbon group, a heteroatom containing group, silicon, germanium, tin, lead, or phosphorus, wherein the Group 15 or 16 atom may also be bound to nothing or a hydrogen, a Group 14 atom containing group, a halogen, or a heteroatom containing group, and wherein each of the two Group 15 atoms are also bound to a cyclic group and may optionally be bound to hydrogen, a halogen, a heteroatom or a hydrocarbyl group, or a heteroatom containing group.

In another embodiment, the Group 15 containing metal catalyst compound, prepared by the method of the present invention is represented by the formulae:

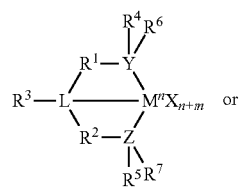

(V)

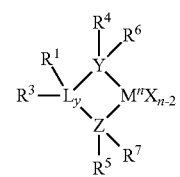

(VI)

wherein: M is a Group 3 to 12 transition metal or a Group 13 or 14 main group metal, preferably a Group 4, 5, or 6 metal, and more preferably a Group 4 metal, and most preferably zirconium, titanium or hafnium; each X is independently a leaving group, preferably, an anionic leaving group, and more preferably hydrogen, a hydrocarbyl group, a heteroatom or a halogen, and most preferably an alkyl; y is 0 or 1 (when y is 0 group L' is absent); n is the oxidation state of M, preferably +3, +4, or +5, and more preferably +4; m is the formal charge of the YLZ or the YL'Z ligand, preferably 0, −1, −2 or −3, and more preferably −2; L is a Group 15 or 16 element, preferably nitrogen; L' is a Group 15 or 16 element or Group 14 containing group, preferably carbon, silicon or germanium; Y is a Group 15 element, preferably nitrogen or phosphorus, and more preferably nitrogen; Z is a Group 15 element, preferably nitrogen or phosphorus, and more preferably nitrogen; $R^1$ and $R^2$ are independently a $C_1$ to $C_1$ hydrocarbon group, a heteroatom containing group having up to twenty carbon atoms, silicon, germanium, tin, lead, or phosphorus, preferably a $C_2$ to $C_{20}$ alkyl, aryl or aralkyl group, more preferably a linear, branched or cyclic $C_2$ to $C_{20}$ alkyl group, most preferably a $C_2$ to $C_6$ hydrocarbon group; $R^3$ is absent or a hydrocarbon group, hydrogen, a halogen, a heteroatom containing group, preferably a linear, cyclic or branched alkyl group having 1 to 20 carbon atoms, more preferably $R^3$ is absent, hydrogen or an alkyl group, and most preferably hydrogen; $R^4$ and $R^5$ are independently an alkyl group, an aryl group, substituted aryl group, a cyclic alkyl group, a substituted cyclic alkyl group, a cyclic aralkyl group, a substituted cyclic aralkyl group or multiple ring system, preferably having up to 20 carbon atoms, more preferably between 3 and 10 carbon atoms, and even more preferably a $C_1$ to $C_{20}$ hydrocarbon group, a $C_1$ to $C_{20}$ aryl group or a $C_1$ to $C_{20}$ aralkyl group, or a heteroatom containing group, for example $PR_3$, where R is an alkyl group, $R^1$ and $R^2$ may be interconnected to each other, and/or $R^4$ and $R^5$ may be interconnected to each other; $R^6$ and $R^7$ are independently absent, or hydrogen, an alkyl group, halogen, heteroatom or a hydrocarbyl group, preferably a linear, cyclic or branched alkyl group having 1 to 20 carbon atoms, more preferably absent; and $R^*$ is absent, or is hydrogen, a Group 14 atom containing group, a halogen, a heteroatom containing group.

By "formal charge of the YLZ or YL'Z ligand" it is meant the charge of the entire ligand absent the metal and the leaving groups X.

By "$R^1$ and $R^2$ may also be interconnected" it is meant that $R^1$ and $R^2$ may be directly bound to each other or may be bound to each other through other groups. By "$R^4$ and $R^5$ may also be interconnected" it is meant that $R^4$ and $R^5$ may be directly bound to each other or may be bound to each other through other groups.

An alkyl group may be a linear, branched alkyl radicals, or alkenyl radicals, alkynyl radicals, cycloalkyl radicals or aryl radicals, acyl radicals, aroyl radicals, alkoxy radicals, aryloxy radicals, alkylthio radicals, dialkylamino radicals, alkoxycarbonyl radicals, aryloxycarbonyl radicals, carbomoyl radicals, alkyl- or dialkyl-carbamoyl radicals, acyloxy radicals, acylamino radicals, aroylamino radicals, straight, branched or cyclic, alkylene radicals, or combination thereof. An aralkyl group is defined to be a substituted aryl group.

In a preferred embodiment $R^4$ and $R^5$ are independently a group represented by the following Formula (VII):

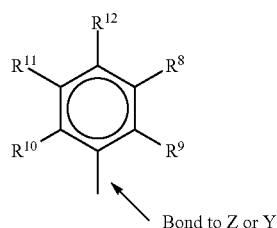

(VII)

wherein $R^8$ to $R^{12}$ are each independently hydrogen, a $C_1$ to $C_{40}$ alkyl group, a halide, a heteroatom, a heteroatom containing group containing up to 40 carbon atoms, preferably a $C_1$ to $C_{20}$ linear or branched alkyl group, preferably a methyl, ethyl, propyl or butyl group, any two R groups may form a cyclic group and/or a heterocyclic group. The cyclic groups may be aromatic. In a preferred embodiment $R^9$, $R^{10}$ and $R^{12}$ are independently a methyl, ethyl, propyl or butyl group (including all isomers), in a preferred embodiment $R^9$, $R^{10}$ and $R^{12}$ are methyl groups, and $R^8$ and $R^{11}$ are hydrogen.

In one particular embodiment, $R^4$ and $R^5$ are both a group represented by the following Formula (VIII):

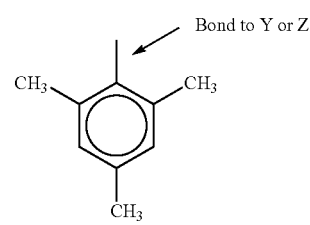

(VIII)

In this embodiment, M is a Group 4 metal, preferably zirconium, titanium or hafnium, and even more preferably zirconium; each of L, Y, and Z is nitrogen; each of $R^1$ and $R^2$ is —$CH_2$—$CH_2$—; $R^3$ is hydrogen; and $R^6$ and $R^7$ are absent.

In a particularly preferred embodiment the Group 15 containing metal catalyst compound, is represented by Compound (IX), below, where Ph denotes a phenyl group:

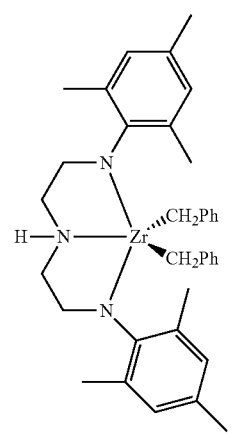

(IX)

In another embodiment, $R^4$ and $R^5$ are both a group represented by the following Formula (X):

(X)

Bond to Y or Z $H_3C$ ... $CH_3$
$H_3C$ ... $CH_3$
$CH_3$

In this embodiment, M is a Group 4 metal, preferably zirconium, titanium or hafnium, and even more preferably zirconium; each of L, Y, and Z is nitrogen; each of $R^1$ and $R^2$ is —$CH_2$—$CH_2$—; $R^3$ is hydrogen; and $R^6$ and $R^7$ are absent.

In a particularly preferred embodiment the Group 15 containing metal catalyst compound, is represented by Compound (XI), below, where Ph denotes a phenyl group:

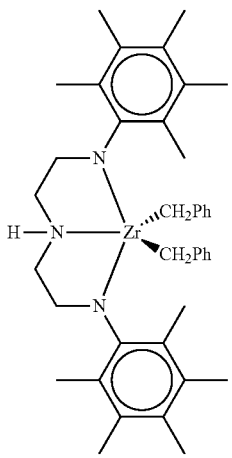

(XI)

Preparation of the Group 15 Atom and Metal Catalyst Compound

The Group 15 atom and metal catalyst compounds may be prepared by reacting the neutral ligand, YLZ or YL'Z, prepared as described above, with a compound represented by the formula M"X$_n$, as is known in the art, where M is a Group 3 to 14 metal, n is the oxidation state of M, each X is independently a leaving group, preferably, an anionic leaving group, and more preferably hydrogen, a hydrocarbyl group, a heteroatom or a halogen, and most preferably an alkyl, in a non-coordinating or weakly coordinating solvent, such as ether, toluene, xylene, benzene, methylene chloride, and/or hexane or other solvent having a boiling point at about 20° C. to about 150° C., and preferably 20° C. to 100° C., preferably for 24 hours or more. When X is a halogen, the mixture is then treated with an excess (such as four or more equivalents) of a strong base, such as for example, lithiumdimethylamide (LiN(CH$_3$)$_2$), or an alkylating agent, such as for example methyl magnesium bromide in ether. The magnesium salts, if present, are removed by filtration. The resulting metal complex is then isolated by standard techniques. In a preferred embodiment the solvent has a boiling point above 60° C., such as toluene, xylene, benzene, and/or hexane. In another embodiment the solvent comprises ether and/or methylene chloride, either being preferable.

For example, in some embodiments, the Group 15 atom and metal catalyst compounds, such as that illustrated in Structure (XI), may be prepared by reacting the neutral ligand, YLZ or YL'Z, prepared as described above, with a compound represented by the formula M"X$_n$ where M is Zr, n is the oxidation state of M, and each X is an anionic group, such as a alkyl.

As another example, in some embodiments, the Group 15 atom and metal catalyst compounds, such as that illustrated in Structure (XI), may be prepared by reacting the neutral ligand, YLZ or YL'Z, prepared as described above, with a compound represented by the formula M"X$_n$, as is known in the art, where M is a Group 3 to 14 metal, n is the oxidation state of M, each X is an anionic group, such as benzyl, in a non-coordinating or weakly coordinating solvent, such as toluene, xylene, benzene, methylene chloride, and/or hexane or other solvent having a boiling point at about 20° C. to about 150° C., and preferably 20° C. to 100° C., preferably for one hour or more. The resulting metal complex can be isolated by removing the solvent and washing the resultant solid with hexane to yield a powder. In a preferred embodiment the solvent for the reaction is toluene.

Activators and Activation Methods for Catalyst Compounds

The Group 15 atom and metal catalyst compounds, prepared above, are typically combined with an activator compound to yield compounds having a vacant coordination site that will coordinate, insert, and polymerize olefin(s). For the purposes of this patent specification and appended claims, the term "activator" is defined to be any compound which can activate any one of the catalyst compounds described above by converting the neutral catalyst compound to a catalytically active catalyst compound cation. Non-limiting activators, for example, include alumoxanes, aluminum alkyls, ionizing activators, which may be neutral or ionic, and conventional-type cocatalysts.

Alumoxane and Aluminum Alkyl Activators

In one embodiment, alumoxanes activators are utilized as an activator in the catalyst composition of the invention. Alumoxanes are generally oligomeric compounds containing —Al(R)—O— subunits, where R is an alkyl group. Examples of alumoxanes include methylalumoxane (MAO), modified methylalumoxane (MMAO), ethylalumoxane and isobutylalumoxane. Alumoxanes may be produced by the hydrolysis of the respective trialkylaluminum compound. MMAO may be produced by the hydrolysis of trimethylaluminum and a higher trialkylaluminum such as triisobutylaluminum. MMAO's are generally more soluble in aliphatic solvents and more stable during storage. There are a variety of methods for preparing alumoxane and modified alumoxanes, non-limiting examples of which are described in U.S. Pat. Nos. 4,665,208, 4,952,540, 5,091,352, 5,206,199, 5,204,419, 4,874,734, 4,924,018, 4,908,463, 4,968,827, 5,308,815, 5,329,032, 5,248,801, 5,235,081, 5,157,137, 5,103,031, 5,391,793, 5,391,529, 5,693,838, 5,731,253, 5,731,451, 5,744,656, 5,847,177, 5,854,166, 5,856,256 and 5,939,346 and European publications EP-A-0 561 476, EP-B1-0 279 586, EP-A-0 594-218 and EP-B1-0 586 665, and PCT publications WO 94/10180 and WO 99/15534, all of which are herein fully incorporated by reference. A another alumoxane is a modified methyl alumoxane (MMAO) cocatalyst type 3A (commercially available from Akzo Chemicals, Inc. under the trade name Modified Methylalumoxane type 3A, covered under patent number U.S. Pat. No. 5,041,584).

Aluminum alkyl or organoaluminum compounds which may be utilized as activators include trimethylaluminum, triethylaluminum, triisobutylaluminum, tri-n-hexylaluminum, tri-n-octylaluminum and the like.

Ionizing Activators

It is within the scope of this invention to use an ionizing or stoichiometric activator, neutral or ionic, such as tri (n-butyl) ammonium tetrakis (pentafluorophenyl) boron, a trisperfluorophenyl boron metalloid precursor or a trisperfluoronaphtyl boron metalloid precursor, polyhalogenated heteroborane anions (WO 98/43983), boric acid (U.S. Pat. No. 5,942,459) or combination thereof. It is also within the scope of this invention to use neutral or ionic activators alone or in combination with alumoxane or modified alumoxane activators.

Examples of neutral stoichiometric activators include trisubstituted boron, tellurium, aluminum, gallium and indium or mixtures thereof. The three substituent groups are each independently selected from alkyls, alkenyls, halogen, substituted alkyls, aryls, arylhalides, alkoxy and halides. Preferably, the three groups are independently selected from halogen, mono or multicyclic (including halosubstituted) aryls, alkyls, and alkenyl compounds and mixtures thereof, preferred are alkenyl groups having 1 to 20 carbon atoms, alkyl groups having 1 to 20 carbon atoms, alkoxy groups having 1 to 20 carbon atoms and aryl groups having 3 to 20 carbon atoms (including substituted aryls). More preferably, the three groups are alkyls having 1 to 4 carbon groups, phenyl, napthyl or mixtures thereof. Even more preferably, the three groups are halogenated, preferably fluorinated, aryl groups. Most preferably, the neutral stoichiometric activator is trisperfluorophenyl boron or trisperfluoronapthyl boron.

Ionic stoichiometric activator compounds may contain an active proton, or some other cation associated with, but not coordinated to, or only loosely coordinated to, the remaining ion of the ionizing compound. Such compounds and the like are described in European publications EP-A-0 570 982, EP-A-0 520 732, EP-A-0 495 375, EP-B1-0 500 944, EP-A-0 277 003 and EP-A-0 277 004, and U.S. Pat. Nos. 5,153,157, 5,198,401, 5,066,741, 5,206,197, 5,241,025, 5,384,299 and 5,502,124 and U.S. patent application Ser. No. 08/285,380, filed Aug. 3, 1994, all of which are herein fully incorporated by reference.

In a preferred embodiment, the stoichiometric activators include a cation and an anion component, and may be represented by the following formula:

The cation component, $(L-H)_d^+$ may include Bronsted acids such as protons or protonated Lewis bases or reducible Lewis acids capable of protonating or abstracting a moiety, such as an alkyl or aryl, from the metallocene or Group 15 containing transition metal catalyst precursor, resulting in a cationic transition metal species.

The activating cation $(L-H)_d^+$ may be a Bronsted acid, capable of donating a proton to the transition metal catalytic precursor resulting in a transition metal cation, including ammoniums, oxoniums, phosphoniums, silyliums and mixtures thereof, preferably ammoniums of methylamine, aniline, dimethylamine, diethylamine, N-methylaniline, diphenylamine, trimethylamine, triethylamine, N,N-dimethylaniline, methyldiphenylamine, pyridine, p-bromo N,N-dimethylaniline, p-nitro-N,N-dimethylaniline, phosphoniums from triethylphosphine, triphenylphosphine, and diphenylphosphine, oxomiuns from ethers such as dimethyl ether diethyl ether, tetrahydrofuran and dioxane, sulfoniums from thioethers, such as diethyl thioethers and tetrahydrothiophene and mixtures thereof. The activating cation $(L—H)_d^+$ may also be an abstracting moiety such as silver, carboniums, tropylium, carbeniums, ferroceniums and mixtures, preferably carboniums and ferroceniums. Most preferably $(L-H)_d^+$ is triphenyl carbonium.

The anion component $A^{d-}$ include those having the formula $[M^{k+}Q_n]^{d-}$ where k is an integer from 1 to 3; n is an integer from 2-6; n–k=d; M is an element selected from Group 13 of the Periodic Table of the Elements, preferably boron or aluminum, and Q is independently a hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q having up to 20 carbon atoms with the proviso that in not more than 1 occurrence is Q a halide. Preferably, each Q is a fluorinated hydrocarbyl group having 1 to 20 carbon atoms, more preferably each Q is a fluorinated aryl group, and most preferably each Q is a pentafluoryl aryl group. Examples of suitable $A^{d-}$ also include diboron compounds as disclosed in U.S. Pat. No. 5,447,895, which is fully incorporated herein by reference.

Supports, Carriers and General Supporting Techniques

The Group 15 atom and metal catalyst compound, prepared in accordance with the invention may be combined with a support material or carrier, or with a supported activator. For example, the catalyst compound is deposited on, contacted with, vaporized with, bonded to, or incorporated within, adsorbed or absorbed in, or on, a support or carrier.

The support material is any of the conventional support materials. Preferably the supported material is a porous support material, for example, talc, inorganic oxides and inorganic chlorides. Other support materials include resinous support materials such as polystyrene, functionalized or crosslinked organic supports, such as polystyrene divinyl benzene polyolefins or polymeric compounds, zeolites, clays, or any other organic or inorganic support material and the like, or mixtures thereof.

The preferred support materials are inorganic oxides that include those Group 2, 3, 4, 5, 13 or 14 metal oxides. The preferred supports include silica, fumed silica, alumina (WO 99/60033), silica-alumina and mixtures thereof. Other useful supports include magnesia, titania, zirconia, magnesium chloride (U.S. Pat. No. 5,965,477), montmorillonite (European Patent EP-B1 0 511 665), phyllosilicate, zeolites, talc, clays (U.S. Pat. No. 6,034,187) and the like. Also, combinations of these support materials may be used, for example, silica-chromium, silica-alumina, silica-titania and the like. Additional support materials may include those porous acrylic polymers described in EP 0 767 184 B1, which is incorporated herein by reference. Other support materials include nanocomposites as described in PCT WO 99/47598, aerogels as described in WO 99/48605, spherulites as described in U.S. Pat. No. 5,972,510 and polymeric beads as described in WO 99/50311, which are all herein incorporated by reference. A preferred support is fumed silica available under the trade name Cabosil™ TS-610, available from Cabot Corporation. Fumed silica is typically a silica with particles 7 to 30 nanometers in size that has been treated with dimethylsilyldichloride such that a majority of the surface hydroxyl groups are capped.

It is preferred that the support material, most preferably an inorganic oxide, has a surface area in the range of from about 10 to about 700 $m^2/g$, pore volume in the range of from about 0.1 to about 4.0 cc/g and average particle size in the range of from about 5 to about 500 microns. More preferably, the surface area of the support material is in the range of from about 50 to about 500 $m^2/g$, pore volume of from about 0.5 to about 3.5 cc/g and average particle size of from about 10 to about 200 microns. Most preferably the surface area of the support material is in the range is from about 100 to about 400 $m^2/g$, pore volume from about 0.8 to about 3.0 cc/g and average particle size is from about 5 to about 100 microns. The average pore size of the carrier of the invention typically has pore size in the range of from 10 to 1000 Å, preferably 50 to about 500 Å, and most preferably 75 to about 350 Å.

Polymerization Processes

The catalyst compounds described herein are applicable to any polymerization process, for example, by suspension, solution, slurry, gas phase process, or a combination thereof, using known equipment and reaction conditions, and is not limited to any specific type of polymerization system. Thus, the catalyst compounds described herein may also have applicability to many types of processes, including but not limited to, gas phase, gas/solid phase, liquid/solid phase, gas/liquid phase, and gas/liquid/solid phase reactor systems including polymerization reactor systems; gas phase, gas/solid phase, liquid/solid phase, gas/liquid phase, and gas/liquid/solid phase mass transfer systems; gas phase, gas/solid phase, liquid/solid phase, gas/liquid phase, and gas/liquid/solid phase mixing systems; gas phase, gas/solid phase, liquid/solid phase, gas/liquid phase, and gas/liquid/solid phase heating or cooling systems; gas/solid phase and gas/solid/liquid phase drying systems; etc.

EXAMPLES

It is to be understood that while the invention has been described in conjunction with the specific embodiments thereof, the foregoing description is intended to illustrate and not limit the scope of the invention. Other aspects, advantages and modifications will be apparent to those skilled in the art to which the invention pertains.

General Procedure for the Palladium-Catalyzed Coupling of Diethylenetriamine and 2,3,4,5,6-Pentamethylbromobenzene Examples 1 and Comparative Examples 1-25

In a drybox, palladium precatalyst (0.01 mmol), ligand (0.01 mmol), 2,3,4,5,6-pentamethylbromobenzene (227.0 mg, 1.00 mmol), diethylenetriamine (56.7 µL, 0.52 mmol), sodium tert-butoxide (120.1 mg, 1.25 mmol), dodecane (50.0 µL, 0.020 mmol), and 1 mL of solvent were added to a 4 mL scintillation vial equipped with a magnetic stir bar and sealed with a cap containing a PTFE septum. Reactions were placed into a temperature controlled aluminum heating block and samples were taken at various time points and analyzed by GC/MS. Conversions were determined relative to an internal standard (dodecane).

Example 1

The palladium catalyzed coupling of 2 equivalents of 2,3,4,5,6-pentamethylbromobenzene (PMBB) and diethylenetriamine (DETA) to selectively yield. $N^1$-(2,3,4,5,6-pentamethylphenyl)-$N^2$-(2-(2,3,4,5,6-pentamethylphenylamino)ethyl)ethane-1,2-diamine (reaction IV above) was performed using a palladium complex with CyPF-t-Bu. The palladium complex with CyPF-t-Bu was formed using a palladium acetate (Pd(OAc)$_2$) as a catalyst precursor.

Comparative Examples 1-25

The reactive coupling of DETA and PMBB was performed using comparative palladium catalysts as shown in Table 1, formed from the listed palladium precursor and ligand. The abbreviated ligands shown in Table 1 are detailed in the Table 1 Key.

For each of Example 1 and Comparative Examples 2-23, the reaction was performed using approximately 1 mole percent catalyst, 2.5 equivalents of base (NaO$^t$Bu), dodecane as an internal standard, in a solvent, where the reaction was performed at 100° C. Reaction conditions for Comparative Example 1 included 1 mole percent palladium, 1 mole percent ligand, 1 mmol PMBB, 0.5 mmol DETA, 1.25 mmol NaO$^t$Bu, and 1 mL solvent, where the reaction was performed at 25° C.

TABLE 1

| Reaction | Pd Precursor | Ligand | Solvent | Time (h) | Conversion (%) |
|---|---|---|---|---|---|
| Example 1 | Pd(OAc)$_2$ | CyPF-t-Bu | DME | 0.25 | 99.6 |
| Comp. Ex. 1 | (SiPr)Pd(allyl)Cl | CyPF-t-Bu | DME | 0.5 | 65.3 |
| Comp. Ex. 2 | (SiPr)Pd(allyl)Cl | CyPF-t-Bu | DME | 2.0 | 66.5 |
| Comp. Ex. 3 | Pd$_2$dba$_3$ | Binap | Toluene | 2 | 80.2 |
| Comp. Ex. 4 | Pd$_2$dba$_3$ | Binap | Toluene | 3.5 | 93.2 |
| Comp. Ex. 5 | Pd$_2$dba$_3$ | 15-1048 | Toluene | 2 | 0.0 |
| Comp. Ex. 6 | Pd(OAc)$_2$ | 15-1048 | Toluene | 2 | 8.4 |

TABLE 1-continued

| Reaction | Pd Precursor | Ligand | Solvent | Time (h) | Conversion (%) |
|---|---|---|---|---|---|
| Comp. Ex. 7 | Pd$_2$dba$_3$ | 15-1052 | Toluene | 2 | 6.3 |
| Comp. Ex. 8 | Pd(OAc)$_2$ | 15-1052 | Toluene | 2 | 7.1 |
| Comp. Ex. 9 | Pd$_2$dba$_3$ | 15-2975 | Toluene | 2 | 4.3 |
| Comp. Ex. 10 | Pd(OAc)$_2$ | 15-2975 | Toluene | 2 | 11.1 |
| Comp. Ex. 11 | Pd$_2$dba$_3$ | 15-1145 | Toluene | 0.5 | 61.2 |
| Comp. Ex. 12 | Pd$_2$dba$_3$ | 15-1145 | Toluene | 2 | 68.3 |
| Comp. Ex. 13 | Pd(OAc)$_2$ | 15-1145 | Toluene | 2 | 34.3 |
| Comp. Ex. 14 | Pd$_2$dba$_3$ | 15-1149 | Toluene | 2 | 6.3 |
| Comp. Ex. 15 | Pd(OAc)$_2$ | 15-1149 | Toluene | 2 | 8.5 |
| Comp. Ex. 16 | Pd$_2$dba$_3$ | 15-2980 | Toluene | 2 | 4.3 |
| Comp. Ex. 17 | Pd(OAc)$_2$ | 15-2980 | Toluene | 2 | 12.0 |
| Comp. Ex. 18 | Pd$_2$dba$_3$ | 15-0380 | Toluene | 2 | 0.9 |
| Comp. Ex. 19 | Pd(OAc)$_2$ | 15-0380 | Toluene | 2 | 4.7 |
| Comp. Ex. 20 | Pd$_2$dba$_3$ | 15-1242 | Toluene | 2 | 26.3 |
| Comp. Ex. 21 | Pd(OAc)$_2$ | 15-1242 | Toluene | 2 | 6.1 |
| Comp. Ex. 22 | Pd$_2$dba$_3$ | 26-0275 | Toluene | 2 | 7.6 |
| Comp. Ex. 23 | Pd(OAc)$_2$ | 26-0275 | Toluene | 2 | 11.1 |
| Comp. Ex. 24 | 46-0272 | — | Toluene | 2 | 25.8 |
| Comp. Ex. 25 | 46-0025 | — | Toluene | 2 | 5.2 |

Table 1 Key:

(SiPr)Pd(allyl)Cl

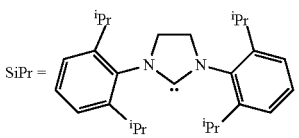

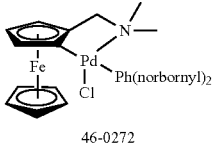

46-0272

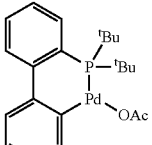

46-0025

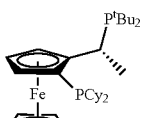

CyPF-t-Bu

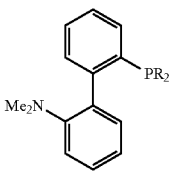

R = $^t$Bu: 15-1048
Cy: 15-1145

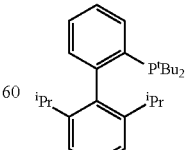

R = $^t$Bu: 15-1052
Cy: 15-1149

TABLE 1-continued

| Reaction | Pd Precursor | Ligand | Solvent | Time (h) | Conversion (%) |
|---|---|---|---|---|---|

Ligand structures:

- N-(2-methoxyphenyl)pyrrole with P$^t$Bu$_2$ substituent
  - R = $^t$Bu: 15-2975
  - Cy: 15-2980
- Bis(2-(diphenylphosphino)phenyl) ether (PPh$_2$, O, PPh$_2$): 15-0380
- Xantphos (9,9-dimethyl-4,5-bis(diphenylphosphino)xanthene): 15-1242
- 1,1'-Bis(diisopropylphosphino)ferrocene (P$^i$Pr$_2$, Fe, P$^i$Pr$_2$): 26-0275

As shown by the experimental results, the catalyst system of Pd(OAc)$_2$/CyPF-t-Bu (Example 1) exhibits increased rates in comparison to the catalyst systems of U.S. Pat. No. 6,518,444 (Table 1, entries 1 and 2) and outperforms all other catalyst systems surveyed while maintaining excellent selectivity (>98%) for the desired product. The benchmark catalyst system composed of Pd$_2$dba$_3$ and rac-Binap performed as expected; after 3.5 hours the reaction yielded the desired product in 93.2% (Table 1, Comparative Examples 3 and 4). Catalyst systems based on bulky monodendate phosphines (Comparative Examples 5-10 and 14-17) and wide bite-angle bidendate phosphines (Comparative Examples 18-23) with either Pd$_2$dba$_3$ or Pd(OAc)$_2$ proved to be inefficient, yielding less than 26.3% of the desired product after 2 hours at 100° C. Cyclometallated palladium complexes (entries 25 and 26) also proved unproductive. Modest yields were achieved with Comparative Example 11 and Comparative Example 1, although extended reaction times proved, for both catalysts, that catalyst decomposition limited conversion. The catalyst system according to embodiments disclosed herein, CyPF-t-Bu and Pd(OAc)$_2$ demonstrated the highest activity of any catalyst sampled, and the catalyst afforded the desired product in quantitative yield in only 15 minutes (Example 1).

General Procedure for the Effect of Catalyst Concentration on the Palladium-Catalyzed Coupling of Diethylenetriamine and 2,3,4,5,6-Pentamethylbromobenzene Examples 2-6 and Comparative Example 26

In a drybox, 2,3,4,5,6-pentamethylbromobenzene (227.0 mg, 1.00 mmol), diethylenetriamine (56.7 µL, 0.52 mmol), sodium tert-butoxide (120.1 mg, 1.25 mmol), dodecane (50.0 µL, 0.020 mmol), and 1 mL of solvent were added to a 4 mL scintillation vial equipped with a magnetic stirbar. An aliquot of a freshly prepared 10.0 mM solution of Pd(OAc)$_2$/CyPF-t-Bu was added and the reaction was sealed with a cap containing a PTFE septum. Reactions were placed into a temperature controlled aluminum heating block and samples were taken a various time points and analyzed by GC/MS. Conversions were determined relative to an internal standard (dodecane).

Examples 2-6

The effect of reducing the catalyst loading was investigated. Reaction profiles were monitored by GC while varying catalyst concentrations between 0.025 and 1.0 mol % at similar conditions as given for Example 1. Catalyst concentrations for each Example are given in Table 2.

TABLE 2

| Reaction | Mol % Pd(OAc)$_2$/CyPF—t-Bu |
|---|---|
| Example 1 | 1.0 |
| Example 2 | 0.5 |
| Example 3 | 0.1 |
| Example 4 | 0.075 |
| Example 5 | 0.05 |
| Example 6 | 0.025 |

Comparative Example 26

The reduced catalyst loading of Examples 1-6 were compared to a reaction performed with 1.0 mol % Pd$_2$(dba)$_3$/2.0 mol % rac-Binap, also performed at similar conditions as given for Comparative Example 3.

Samples were taken periodically during the duration of the reaction and analyzed for conversion of the reactants to the N-aryl amine. Conversion versus time results for the reactions is shown in FIG. 1. The reaction analyses clearly indicate that the Pd(OAc)$_2$/CyPF-t-Bu, even at the reduced loading, had better activity than the catalyst of Comparative Example 26.

Reactions conducted with 1.0 or 0.5 mol % catalyst (Examples 1 and 2) were indistinguishable, reaching complete conversion by the first data point. Subsequent reactions with reduced catalyst loadings were distinguishable; reactions conducted with 0.1 mol % (Example 3), 0.075 mol % (Example 4), and 0.05 mol % (Example 5) reached complete conversion at 60 minutes, 180 minutes, and >180 minutes, respectively. Interestingly, reducing the catalyst concentration to 0.025 mol % resulted in failure to achieve complete conversion even with prolonged reaction times, presumably due to catalyst decomposition.

Examples 7-11

Coupling reactions using catalyst compositions according to embodiments disclosed herein was also conducted at a larger scale, at approximately 250 time the scale of Example 1. The only notable change in procedure as compared to Example 1, to facilitate an easier workup, was the devolatilization of the reaction solvent prior to partitioning between an aqueous/organic system. In addition to the amination of PMBB with diethylenetriamene, the arylation of 1,5-diaminopentane and 2,2'-oxydimethylamine were also investigated. Experimental procedures are given below for each Example, followed by a summary of results in Table 3.

Large Scale Preparation of N1-(2,3,4,5,6-pentamethylphenyl)-N2-(2-(2,3,4,5,6-pentamethylphenylamino)ethyl)ethane-1,2-diamine Example 7

In a drybox, 2,3,4,5,6-pentamethylbromobenzene (57.50 g, 253.2 mmol), sodium tert-butoxide (30.41 g, 316.4 mmol), 250 mL of anhydrous DME, and diethylenetriamine (13.81 mL, 127.8 mmol) were combined in an oven-dried 500 mL round bottom flask equipped with a magnetic stirbar. Pd(OAc)$_2$ (14.2 mg, 0.0632 mmol), CyPF-t-Bu (35.1 mg, 0.0633 mmol), and DME (dimethyl ether, 2 mL) were combined in a separate 4 mL scintillation vial and stirred until homogenous before addition to the former solution. A reflux condenser was fitted to the reaction which was subsequently heated to 100° C. overnight (14 h). After cooling the reaction to room temperature complete conversion was confirmed by GC/MS. All volatiles were removed by rotary evaporation and the residue was partitioned between 400 mL H2O/CH2Cl2 (1:1). The organic fraction was separated and the aqueous phase washed with two 50 mL portions of CH2Cl2. The organic fractions were combined and dried over MgSO4. The suspension was filtered and all volatile materials were removed by rotary evaporation to afford N1-(2,3,4,5,6-pentamethylphenyl)-N2-(2-(2,3,4,5,6-pentamethylphenylamino)ethyl)ethane-1,2-diamine (49.79 g, 99.4%) as a light tan solid.

$^1$H NMR spectra were obtained at 400 MHz and recorded relative to residual protio solvent. $^{13}$C NMR spectra were obtained at 101 MHz and recorded relative to the residual solvent resonance. The spectra recorded are as follows: $^1$H NMR (CDCl$_3$, 400 MHz, 22° C.): δ 2.34 (s, 6H), 2.36 (s, 12H), 2.42 (s, 12H), 3.02-3.05 (m, 4H), 3.09-3.12 (m, 4H). $^{13}$C NMR (CDCl$_3$, 101 MHz, 22° C.): δ 14.8, 16.4, 16.7, 49.4, 50.0, 126.8, 129.5, 132.8, 143.5.

N1,N5-bis(2,3,4,5,6-pentamethylphenyl)pentane-1,5-diamine

Example 8

In a drybox, 2,3,4,5,6-pentamethylbromobenzene (750.0 mg, 3.30 mmol), 1,5-pentanediamine (195.2 μL, 1.67 mmol), sodium tertbutoxide (396.6 mg, 4.13 mmol), 3.0 mL of dimethyoxyethane, and 10.0 mM Pd(OAc)$_2$/CyPF-t-Bu (82.5 μL, 8.25×10-4 mmol) were added to a 20 mL scintillation vial equipped with a magnetic stirbar and sealed with a cap containing a PTFE septum. The reaction was placed into a temperature controlled aluminum heating block and stirred at 100° C. for 6 h. After cooling to room temperature, the reaction mixture was partitioned between 100 mL H2O/Diethyle ether (Et2O) (1:1), the organic phase separated and dried over MgSO4, followed by the removal of all volatiles to afford 619 mg (95.0%) of the title compound.

$^1$H NMR spectra were obtained at 400 MHz and recorded relative to residual protio solvent. $^{13}$C NMR spectra were obtained at 101 MHz and recorded relative to the residual solvent resonance. The spectra recorded are as follows: $^1$H NMR (CDCl$_3$, 400 MHz, 22° C.): δ 1.50-1.71 (m, 6H), 2.21 (s, 6H), 2.22 (s, 12H), 2.25 (s, 12H), 2.84 (t, J=7.2 Hz, 4H), 2.88 (br s, 2H). $^{13}$C NMR (CDCl3, 101 MHz, 22° C.): δ 14.8, 16.5, 16.9, 25.0, 30.9, 49.9, 126.8, 129.6, 132.9, 143.7.

N,N'-(2,2'-oxybis(ethane-2,1-diyl))bis(2,3,4,5,6-pentamethylaniline)

Example 9

In a drybox, 2,3,4,5,6-pentamethylbromobenzene (750.0 mg, 3.30 mmol), 2,2'-oxydiethylamine dihydrochloride (295.3 mg, 1.67 mmol), sodium tert-butoxide (714.0 mg, 7.43 mmol), 3.0 mL of dimethyoxyethane, and 10.0 mM Pd(OAc)$_2$/CyPF-t-Bu (82.5 μL, 8.25×10-4 mmol) were added to a 20 mL scintillation vial equipped with a magnetic stirbar and sealed with a cap containing a PTFE septum. The reaction was placed into a temperature controlled aluminum heating block and stirred at 100° C. for 6 h. After cooling to room temperature, the reaction mixture was partitioned between 100 mL H2O/Et2O (1:1), the organic phase separated and dried over MgSO4, followed by the removal of all volatiles to afford 611 mg (93.3%) of the title compound.

$^1$H NMR spectra were obtained at 400 MHz and recorded relative to residual protio solvent. $^{13}$C NMR spectra were obtained at 101 MHz and recorded relative to the residual solvent resonance. The spectra recorded are as follows: $^1$H NMR (CDCl$_3$, 400 MHz, 22° C.): δ 2.22 (s, 6H), 2.23 (s, 12H), 2.29 (s, 12H), 3.07 (t, J=5.0 Hz, 4H), 3.55 (br s, 2H), 3.67 (t, J=5.0 Hz, 4H). $^{13}$C NMR (CDCl$_3$, 101 MHz, 22° C.): δ 14.7, 16.6, 16.8, 49.3, 70.6, 127.0, 129.7, 133.0, 143.1.

N1,N5-dimesitylpentane-1,5-diamine

Example 10

In a drybox, 2,4,6-trimethylbromobenzene (750.0 μL, 4.90 mmol), 1,5-pentanediamine (286.8 μL, 2.45 mmol), sodium tert-butoxide (588.7 mg, 6.13 mmol), 4.0 mL of dimethyoxyethane, and 10.0 mM Pd(OAc)$_2$/CyPF-t-Bu (123 1.23×10$^{-3}$ mmol) were added to a 20 mL scintillation vial equipped with a magnetic stirbar and sealed with a cap containing a PTFE septum. The reaction was placed into a temperature controlled aluminum heating block and stirred at 100° C. for 6 h. After cooling to room temperature, the reaction mixture was partitioned between 100 mL H2O/Et2O (1:1), the organic phase separated and dried over MgSO4, followed by the removal of all volatiles to afford 821 mg (99.0%) of the title compound.

$^1$H NMR spectra were obtained at 400 MHz and recorded relative to residual protio solvent. $^{13}$C NMR spectra were obtained at 101 MHz and recorded relative to the residual solvent resonance. The spectra recorded are as follows: $^1$H NMR (CDCl$_3$, 400 MHz, 22° C.): δ 1.45-1.54 (m, 2H), 1.59-1.67 (m, 4H), 2.24 (s, 6H), 2.26 (s, 12H), 2.87 (br s, 2H), 2.95 (t, J=7.2 Hz, 4H), 6.83 (s, 4H). $^{13}$C NMR (CDCl3, 101 MHz, 22° C.): δ 18.3, 20.5, 24.8, 31.0, 48.8, 129.4, 129.5, 131.1, 143.7.

N,N'-(2,2'-oxybis(ethane-2,1-diyl))bis(2,4,6-trimethylaniline)

Example 11

In a drybox, 2,4,6-trimethylbromobenzene (500.0 μL, 3.27 mmol), 2,2'-oxydiethylamine dihydrochloride (289.3 mg, 1.63 mmol), sodium tert-butoxide (706.5 mg, 7.35 mmol), 4.0 mL of dimethyoxyethane, and 10.0 mM Pd(OAc)$_2$/CyPF-t-Bu (81.8 μL, 8.18×10-4 mmol) were added to a 20 mL scintillation vial equipped with a magnetic stirbar and sealed with a cap containing a PTFE septum. The reaction was placed into a temperature controlled aluminum heating block and stirred at 100° C. for 6 h. After cooling to room temperature, the reaction mixture was partitioned between 100 mL H2O/Et2O (1:1), the organic phase separated and dried over MgSO4, followed by the removal of all volatiles to afford 505 mg (91.0%) of the title compound.

$^1$H NMR spectra were obtained at 400 MHz and recorded relative to residual protio solvent. $^{13}$C NMR spectra were obtained at 101 MHz and recorded relative to the residual solvent resonance. The spectra recorded are as follows: $^1$H NMR (CDCl3, 400 MHz, 22° C.): δ 2.24 (s, 6H), 2.28 (s, 12H), 3.15 (t, J=5.0 Hz, 4H), 3.49 (br s), 3.61 (t, J=5.0 Hz, 4H), 6.84 (s, 4H). $^{13}$C NMR (CDCl3, 101 MHz, 22° C.): δ 18.2, 20.5, 48.2, 70.4, 129.4, 129.8, 131.3, 143.1.

TABLE 3

| Example | Aryl Bromide | Diamine | Yield % |
|---|---|---|---|
| 7 | PMBB | diethylenetriamine | 99.4 |
| 8 | PMBB | 1,5-diaminopentane | 95.0 |
| 9 | PMBB | 2,2'-oxydiethylamine | 93.3 |
| 10 | TMBB | 1,5-diaminopentane | 99.0 |
| 11 | TMBB | 2,2'-oxydiethylamine | 91.0 |

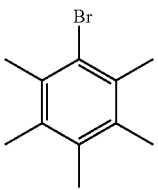
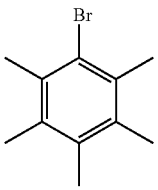
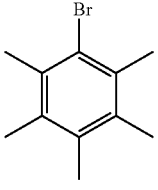
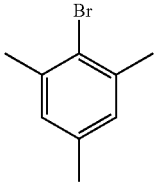
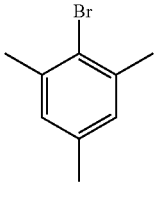

As shown by the above results, the larger scale amination of PMBB with diethylenetriamine was successfully performed at more than 250 time the scale of Example 1, without sacrificing yield or selectivity. Additionally, the arylation of both diamines (1,5-diaminopentane and 2,2'-oxydiethylamine) with either PMBB or 2,4,6-trimethylbromobenzene proceeded cleanly, affording the desired arylated diamines in near quantitative yields.

As described above, Group 8 transition metal catalysts complexes with CyPF-t-Bu may be used to effectively catalyze reactions between nitrogen-containing compounds and arylating agents to form N-aryl amines, which may be used to form polymerization catalysts. In particular, it has been found that palladium acetate/CyPF-t-Bu complexes may achieve greater than 99% conversion at selectivities of at least 98%, where the high conversions may be achieved at reaction times significantly lower than that required by comparative palladium catalysts to reach 80 or 90% conversion.

The phrases, unless otherwise specified, "consists essentially of" and "consisting essentially of" do not exclude the presence of other steps, elements, or materials, whether or not, specifically mentioned in this specification, so long as such steps, elements, or materials, do not affect the basic and novel characteristics of the invention, additionally, they do not exclude impurities and variances normally associated with the elements and materials used.

Only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, within a range includes every point or individual value between its end points even though not explicitly recited. Thus, every point or individual value may serve as its own lower or upper limit combined with any other point or individual value or any other lower or upper limit, to recite a range not explicitly recited.

All documents cited herein are fully incorporated by reference for all jurisdictions in which such incorporation is permitted and to the extent such disclosure is consistent with the description of the present invention.

While the invention has been described with respect to a number of embodiments and examples, those skilled in the art, having benefit of this disclosure, will appreciate that other embodiments can be devised which do not depart from the scope and spirit of the invention as disclosed herein.

What is claimed is:

1. A process for the preparation of N-aryl amine compound N$^1$-(2,3,4,5,6-pentamethylphenyl)-N$^2$-(2-(2,3,4,5,6-pentamethylphenylamino)ethyl)ethane-1,2-diamine, the process comprising:
    reacting a compound having an amino group with an arylating compound in the presence of a base and a transition metal catalyst under reaction conditions effective to form the N-aryl amine compound for a time less than or equal to 180 minutes;
    wherein the transition metal catalyst is present during the reacting at a concentration in the range from about 0.03 to about 1.0 mole percent, based on a total amount of the compound having an amino group, the arylating compound, and the transition metal catalyst;
    wherein the transition metal catalyst is formed by reacting a Group 8 of the Periodic Table metal catalyst precursor comprising palladium (II) acetate (Pd(OAc)$_2$) and at least one chelating ligand comprising (R)-(−)-1-[(S)-2-[dicyclohexylphosphino]-ferrocenyl]ethyldi-t-butylphosphine; and
    wherein the arylating compound comprises at least one compound having the formula:

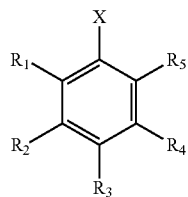

wherein X is a halogen atom or a sulfur-containing leaving group, and $R_1, R_2, R_3, R_4, R_5$ are independently selected from the group consisting of H, CN, alkyl, alkoxy, vinyl, alkenyl, formyl, $CF_3$, $CCl_3$, halide, $C_6H_5$, amide, acyl, ester, alkoxy, amino, thioalkoxy, phosphino, and combinations thereof.

2. The process of claim 1, wherein the compound having an amino group is selected from the primary amine.

3. The process of claim 1, wherein the compound having an amino group comprises diethylenetriamine.

4. The process of claim 1, wherein said arylating compound comprises 2,3,4,5,6-pentamethylbromobenzene.

* * * * *